(12) United States Patent
Tuma

(10) Patent No.: US 7,962,196 B2
(45) Date of Patent: Jun. 14, 2011

(54) METHOD AND SYSTEM FOR DETERMINING THE LOCATION OF A MEDICAL INSTRUMENT RELATIVE TO A BODY STRUCTURE

(75) Inventor: Gregor Tuma, München (DE)

(73) Assignee: Brainlab AG, Feldkirchen (DE)

( * ) Notice: Subject to any disclaimer, the term of this patent is extended or adjusted under 35 U.S.C. 154(b) by 983 days.

(21) Appl. No.: 11/832,731

(22) Filed: Aug. 2, 2007

(65) Prior Publication Data

US 2008/0039716 A1    Feb. 14, 2008

Related U.S. Application Data

(60) Provisional application No. 60/822,713, filed on Aug. 17, 2006.

(30) Foreign Application Priority Data

Aug. 11, 2006 (EP) .................................. 06016809

(51) Int. Cl.
*A61B 5/055* (2006.01)

(52) U.S. Cl. ........................ 600/424; 600/407

(58) Field of Classification Search ........................ None
See application file for complete search history.

(56) References Cited

U.S. PATENT DOCUMENTS

| | | | | |
|---|---|---|---|---|
| 5,295,483 A * | 3/1994 | Nowacki et al. | ............. | 600/439 |
| 5,834,759 A * | 11/1998 | Glossop | ..................... | 250/203.1 |
| 6,135,946 A * | 10/2000 | Konen et al. | .................. | 600/117 |
| 6,187,018 B1 * | 2/2001 | Sanjay-Gopal et al. | ...... | 606/130 |
| 6,385,475 B1 * | 5/2002 | Cinquin et al. | ............... | 600/407 |
| 6,947,783 B2 * | 9/2005 | Immerz | ......................... | 600/410 |
| 7,033,360 B2 * | 4/2006 | Cinquin et al. | ............. | 606/86 R |
| 7,209,776 B2 * | 4/2007 | Leitner | ......................... | 600/407 |
| 7,237,556 B2 * | 7/2007 | Smothers et al. | ............. | 128/898 |
| 7,688,998 B2 * | 3/2010 | Tuma et al. | .................... | 382/103 |
| 7,696,899 B2 * | 4/2010 | Immerz et al. | ........... | 340/825.36 |
| 2001/0025142 A1 * | 9/2001 | Wessels et al. | ............... | 600/425 |
| 2002/0052546 A1 * | 5/2002 | Frantz et al. | .................... | 600/424 |
| 2002/0077543 A1 * | 6/2002 | Grzeszczuk et al. | .......... | 600/424 |
| 2002/0120192 A1 * | 8/2002 | Nolte et al. | .................... | 600/424 |
| 2004/0082849 A1 * | 4/2004 | Schweikard et al. | .......... | 600/424 |
| 2004/0116775 A1 * | 6/2004 | Taniguchi et al. | ............. | 600/117 |
| 2004/0127788 A1 * | 7/2004 | Arata | ............................. | 600/424 |

(Continued)

FOREIGN PATENT DOCUMENTS

| | | |
|---|---|---|
| DE | 103 53 316 | 6/2005 |
| WO | 2005/063139 | 7/2005 |

*Primary Examiner* — Long V Le
*Assistant Examiner* — Angela M Hoffa
(74) *Attorney, Agent, or Firm* — Renner, Otto, Boiselle & Sklar, LLP

(57) ABSTRACT

A method for determining a location of an object relative to a body structure includes: providing a location of a first part of the object relative to a second part of the object, said second part different from said first part; attaching a marker device to the body structure; detecting a location of the marker device relative to the body structure; positioning the object relative to the body structure; detecting a location of the first part of the object relative to the marker device; and calculating a relative location of the second part of the object relative to the location of the body structure based on the location of the first part relative to the second part, the location of the marker device relative to the body structure, and the location of the first part relative to the marker array.

16 Claims, 5 Drawing Sheets

U.S. PATENT DOCUMENTS

| | | |
|---|---|---|
| 2004/0181144 A1 | 9/2004 | Cinquin et al. |
| 2004/0249266 A1* | 12/2004 | Friedrich et al. .............. 600/424 |
| 2005/0027193 A1* | 2/2005 | Mitschke et al. ............. 600/427 |
| 2005/0085714 A1* | 4/2005 | Foley et al. ................... 600/424 |
| 2005/0096535 A1* | 5/2005 | de la Barrera ................ 600/424 |
| 2006/0094958 A1 | 5/2006 | Marquart et al. |

* cited by examiner

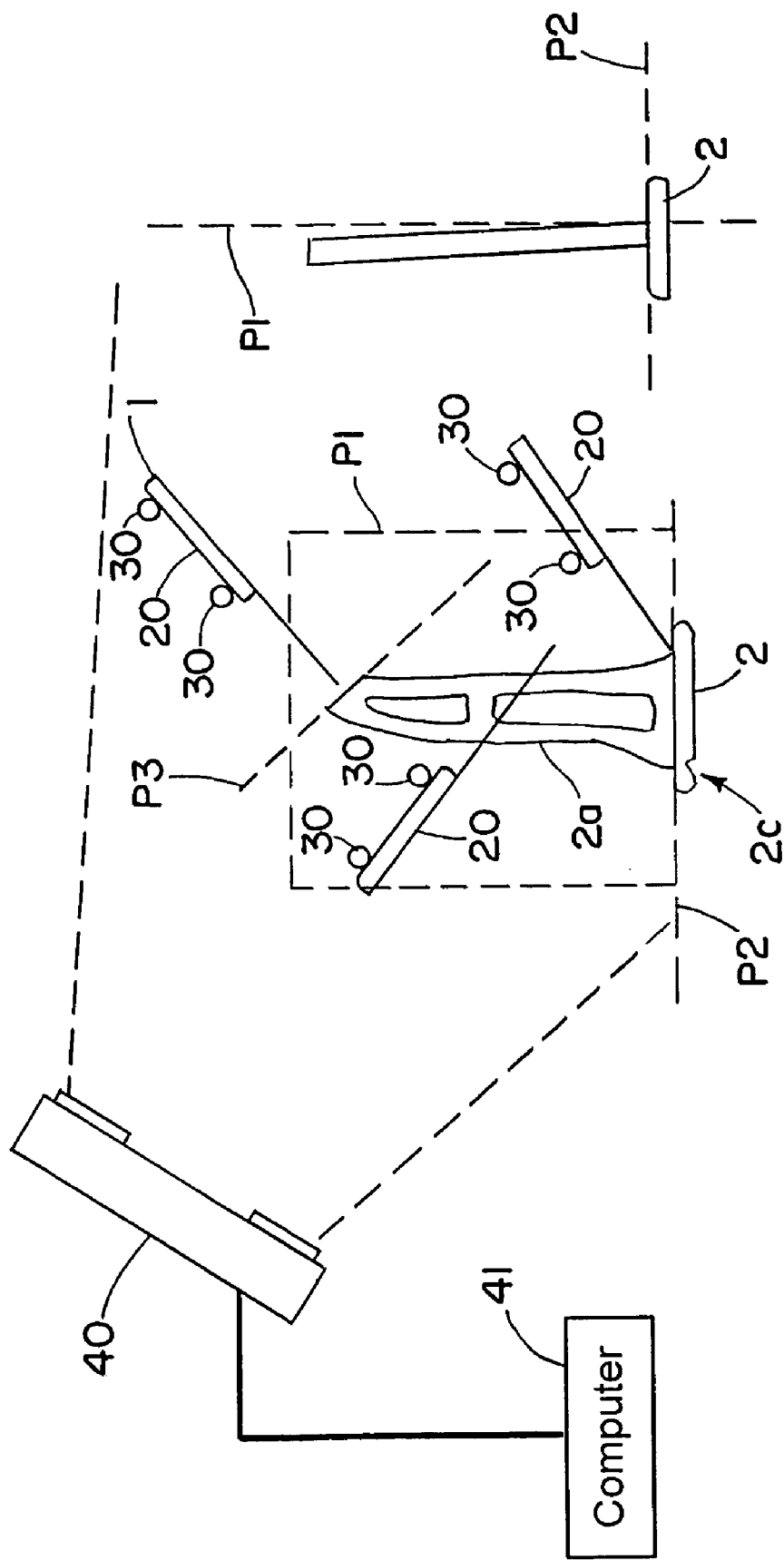

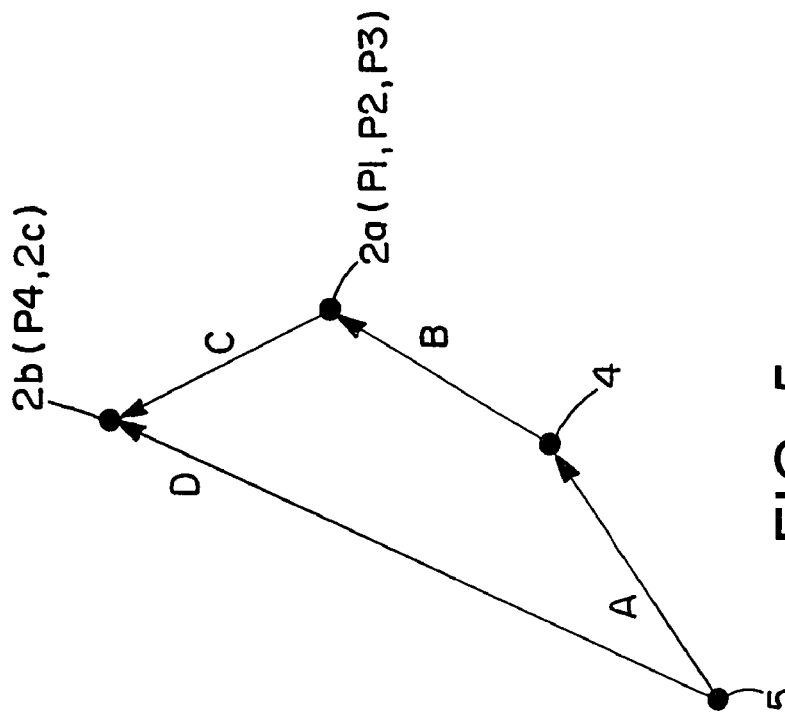
FIG. 5
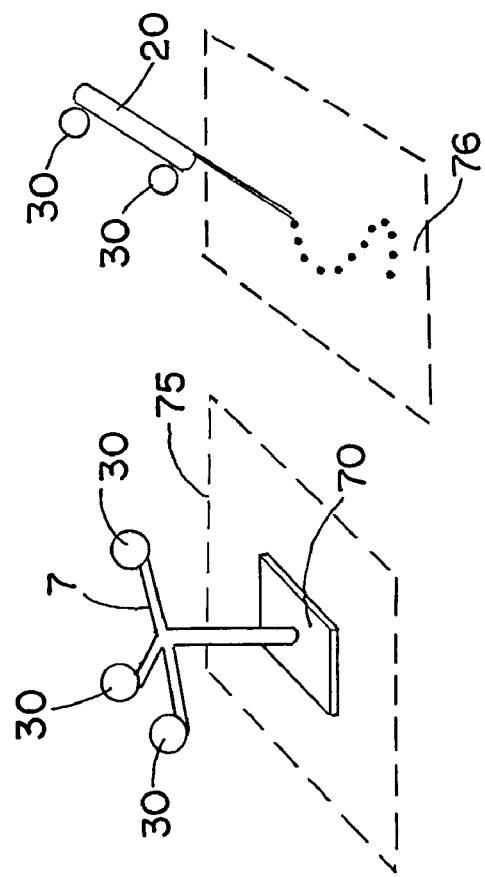
FIG. 4b
FIG. 4a

METHOD AND SYSTEM FOR DETERMINING THE LOCATION OF A MEDICAL INSTRUMENT RELATIVE TO A BODY STRUCTURE

RELATED APPLICATION DATA

This application claims priority of U.S. Provisional Application No. 60/822,713 filed on Aug. 17, 2006, which is incorporated herein by reference in its entirety.

FIELD OF THE INVENTION

The present invention relates to a method and system for determining the location of a medical instrument relative to a body structure.

BACKGROUND OF THE INVENTION

Determining a location of a first object relative to a second object enables a position of the first object (e.g., a medical instrument) that is partially in the second object (e.g., a body structure such as a bone) to also be determined. In the field of medicine, in particular in operations, situations can arise wherein information on the location of a part of an instrument relative to a body structure cannot be directly detected, or only detected with significant difficulty. If, for example, an instrument is introduced into a body structure and the restricted spatial conditions prohibit a marker or reference star from being attached to the instrument, then determining the position of hidden parts of the instrument relative to the body structure becomes problematic.

SUMMARY OF THE INVENTION

The term "body structure" as used here includes bones, cartilage, artificial limbs and/or implants. The term "instrument" as used here includes instruments embodied both in one part (e.g., the instrument consists of a single element) and in a number of parts (e.g., the instrument consists of two or more elements). An instrument is an example of an (exogenous) object. The object, for example, can be a medical instrument, an absorbable implant, or another) body structure. The term "instrument" used below serves as an example of the aforesaid (in particular exogenous) object.

The term "location feature" below refers to a predetermined, in particular characteristic, relative location of a part of an object (e.g., an object or body structure) relative to the location of another part of the same object or relative to the location of a part of another object. The location of a part can be determined by one or more positions of said part in a predetermined reference system. One position can be sufficient to describe the location of a punticular part (e.g., a tip of an instrument). At least two positions can be used to describe the location of an axis. At least three positions can be used to describe the location of a plane.

The aforesaid term "part", for example, can be surface sections (e.g., punticular or in the form of a planar or curved area), planes or axes (e.g., the longitudinal axis of the instrument or of a bone). The positions, for example, can be determined using Cartesian coordinates or spherical coordinates. The location of one part relative to another part can be described by spatial angles and/or distances and/or coordinates (in a reference system) and/or vectors, and the location can be calculated from positions describing the location (e.g., by means of a program running on a computer).

The term "relative location" as used herein, or the expression "location of a first part A relative to a second part B" thus includes the concept of the relative position between the two parts, including punticular parts. If the position of one part is known in a reference system, then on the basis of the relative location of two parts, it is possible to calculate, from the position of one of the two parts, the position of the other of the two parts. This applies to punticular parts. Furthermore, this also includes, for example, the case of the relative location between two parts formed as planes. The relative location, for example, then refers to the angle that the planes assume with respect to each other. For particular purposes, such an angle is sufficient and determining the distance of the planes is not necessarily required. In the case of planes, the term "relative location" need not be restricted to the angle of the planes relative to each other (in particular, the spatial angle), but, for example by defining a center point of the planes, also can include a distance between the center points of the planes. The term "relative location" can include information on the position of two parts relative to each other and/or their orientation and/or their distance relative to each other.

Preferably, at least one location feature of the object is known and can be measured. The location feature or features can be stored, for example, in a data processing system (e.g., a computer).

If the location feature or features of the object and/or the relative location between the first and the second part is not known, or is in particular not stored, then it/they can be determined by means of a measuring device for further processing (in particular, data processing) and in particular also stored. The measuring device can use optical measuring methods in which, for example, the positions of individual parts of the object can be scanned and/or detected (in a particular reference system) by means of pointers. This can be performed by means of a camera, wherein passively reflecting markers or actively emitting markers, which, for example, can be attached to the pointer, may be used. It is also possible to determine the location of parts (e.g., surface sections, points on the surface or planes) relative to other parts, not only using the aforesaid pointers and/or optical measuring methods but also using, for example, ultrasound measurements, NMR (nuclear spin resonance) measurements or x-ray CT measurement, which allow a three-dimensional reconstruction of the object to be calibrated. Equally, the object can be optically recorded three-dimensionally using a number of cameras or movable cameras, in particular on a predetermined measuring table of known dimensions.

Preferably, the object is fixed during measuring. If not, a marker array (e.g., a reference star) can be attached to the object and calibrated therewith, so as to take into account movements of the object to be calibrated.

As already stated above, the relative location of at least two parts of the object can be detected. It is of course also possible to detect the relative location between any other number of parts of the object, such as for example three, four or five parts. Calibrating the location of particular parts of the object relative to one or more other parts does not exclude the possibility of completely calibrating the entire object, in particular determining its outer form not only partially but also completely.

The object can be positioned such that the instrument is situated within the body structure, wherein "within" means that a part of the object is surrounded by the body structure. In particular, the object can be fixed stationary relative to the body structure. In one embodiment, however, a movement of the instrument, for example the instrument tip, also can be tracked using the method and/or device described herein, by repeatedly calibrating a visible part of the instrument.

Where the location of the marker device (e.g., a marker array such as a reference star or individual markers) relative to a body structure is mentioned herein, this refers to the location of the marker relative to predetermined and/or characteristic parts of the body structure (e.g., the location of the individual markers of the marker device relative to the predetermined parts or the predetermined part of the body structure).

BRIEF DESCRIPTION OF THE DRAWINGS

The forgoing and other features of the invention are hereinafter discussed with reference to the drawing.

FIG. 1a is a schematic diagram showing an exemplary assembly for detecting location features of an instrument in accordance with the invention.

FIG. 1b is the lateral view of FIG. 1a.

FIG. 3a shows an exemplary measuring array for calibrating a first part of a two-part instrument in accordance with the invention.

FIG. 3b is a lateral view of FIG. 3a.

FIGS. 4a and 4b show two alternative techniques for calibrating a plane in accordance with the invention.

FIG. 5 schematically shows a chain of exemplary relative locations.

DETAILED DESCRIPTION

The following embodiment illustrates an exemplary implementation of the method described herein. The "bone" referred to in the present embodiment is merely one example of a body structure. The term "body structure" also includes artificial limbs, such that the method enables an instrument to be positioned relative to an artificial limbs, e.g., not necessarily during an operation.

Figure 1:
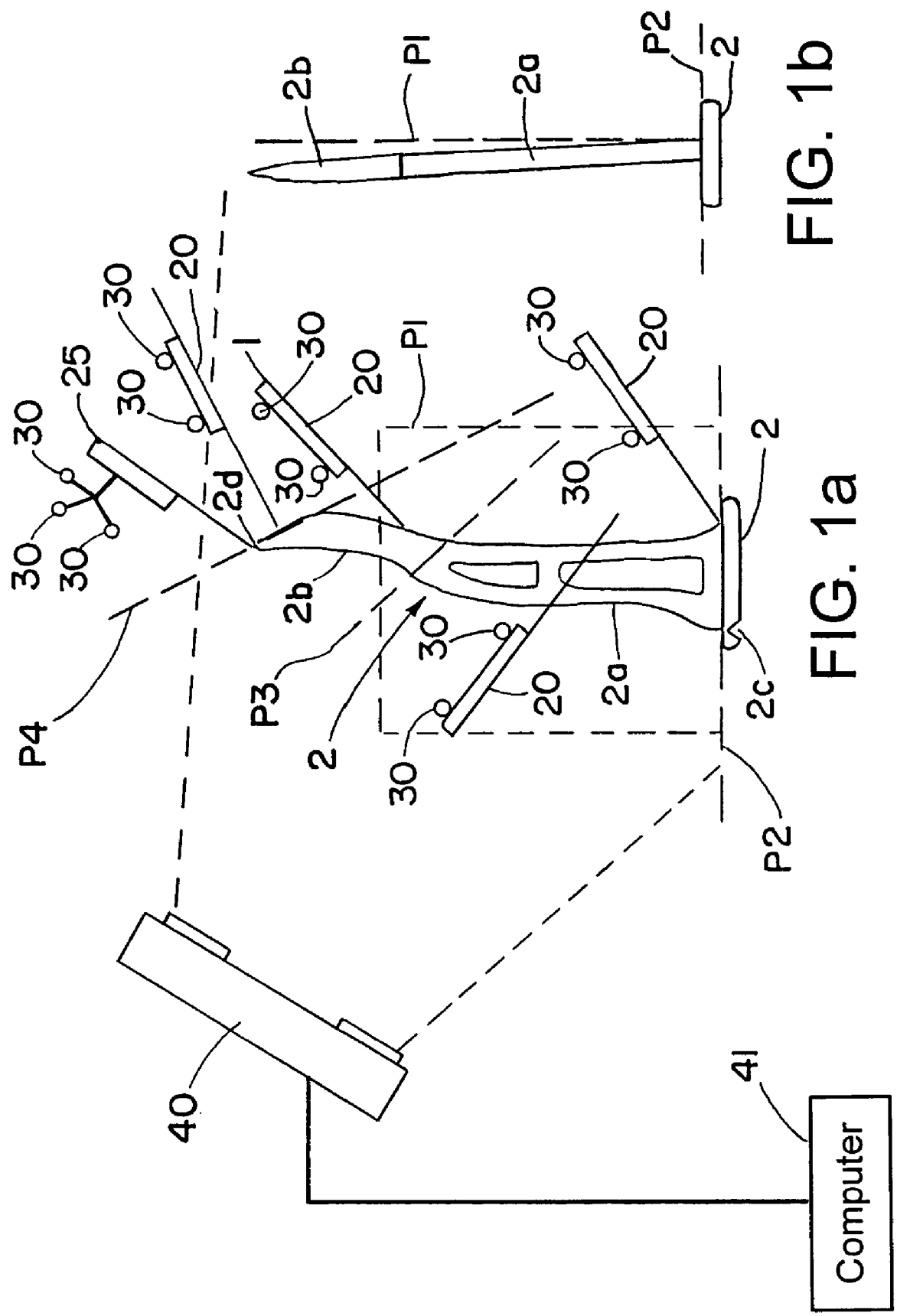

The location features of an instrument, which describe the location of parts of the instrument relative to each other, preferably are stored in advance. FIGS. 1a and 1b show a measuring assembly that enables the location features (not yet stored) of an instrument 2 to be calibrated and then stored. FIG. 1b shows a lateral view of FIG. 1a.

The instrument 2 shown in FIGS. 1a and 1b is a two-part instrument and includes two elements, a first element 2a and a second element 2b. The elements 2a and 2b can be formed as one piece or separate pieces. More particularly, the second element 2b can be detachably coupled to the first element 2a. If the second element 2b is detachably coupled to the first element 2a, then it is preferable that the relative location of elements 2a and 2b is fixed. The instrument 2 can of course also comprise more than two elements.

The instrument 2 also can include one or more recesses 2c for applying a scanning device (e.g., a recess for the tip of a pointer). This can ensure that the same part of the instrument 2 is always scanned. Additionally, the instrument 2 may include protrusions or markings to assist in identifying locations that should be scanned.

As described further below, the instrument 2 can be partially inserted, e.g., the second element 2b can be inserted into a bone. The arrangement in FIG. 1 allows the location features of the instrument 2 to be calibrated. Characteristic planes can be detected, the relative location of which serves as location features that can be determined in the course of an operation, for example, by simply applying a scanning means, such as a so-called pointer 20. The pointer can be viewed as a measuring instrument comprising two marker spheres 30 attached thereto. Calibrating a plane by means of a pointer is explained further below in connection with FIG. 4b.

A detection apparatus 40, which can be operatively coupled to a computational unit 41 (e.g., a computer or the like), can detect light emitted from the markers 30 (the markers are shown by circles and are attached to the pointer 20). The detection apparatus can provide marker position data to the computational unit 41.

The markers 30 can be passive markers which reflect light, or active markers which emit light. In addition to light (in particular, infrared light), other waves or radiation such as for example ultrasound, which can be detected by the detection apparatus 40, also can be used. In the embodiment shown, the detection apparatus 40 is a camera. In addition to a pointer, a laser, for example, also can be used as the scanning means.

The different planes to be calibrated are indicated as P1, P2, P3 and P4. The tip of the pointer 20 is moved in the different planes P1, P2, P3 and P4 in order to spatially detect and/or scan the planes and their location relative to each other. Points of the instrument 2, in particular the tip of the instrument 2, also can be calibrated by means of the tip of a pointer 25 that is provided with a reference star 30. Using the pointer 25, the relative location of the tip of the instrument 2 relative to the other planes can be determined. The instrument 2 preferably is stationary when being calibrated. Alternatively, a reference star, for example, can be fixed to the instrument 2, in order to determine the relative location of the planes or measuring points when the instrument 2 is moved. In particular, the method can be used with instruments in which markers and/or a reference star cannot be attached, or can be attached with difficulty. A measuring device for calibrating the instrument 2 can include a scanning means, such as pointers 20 and/or markers 30, and a detection apparatus 40.

Figure 2:
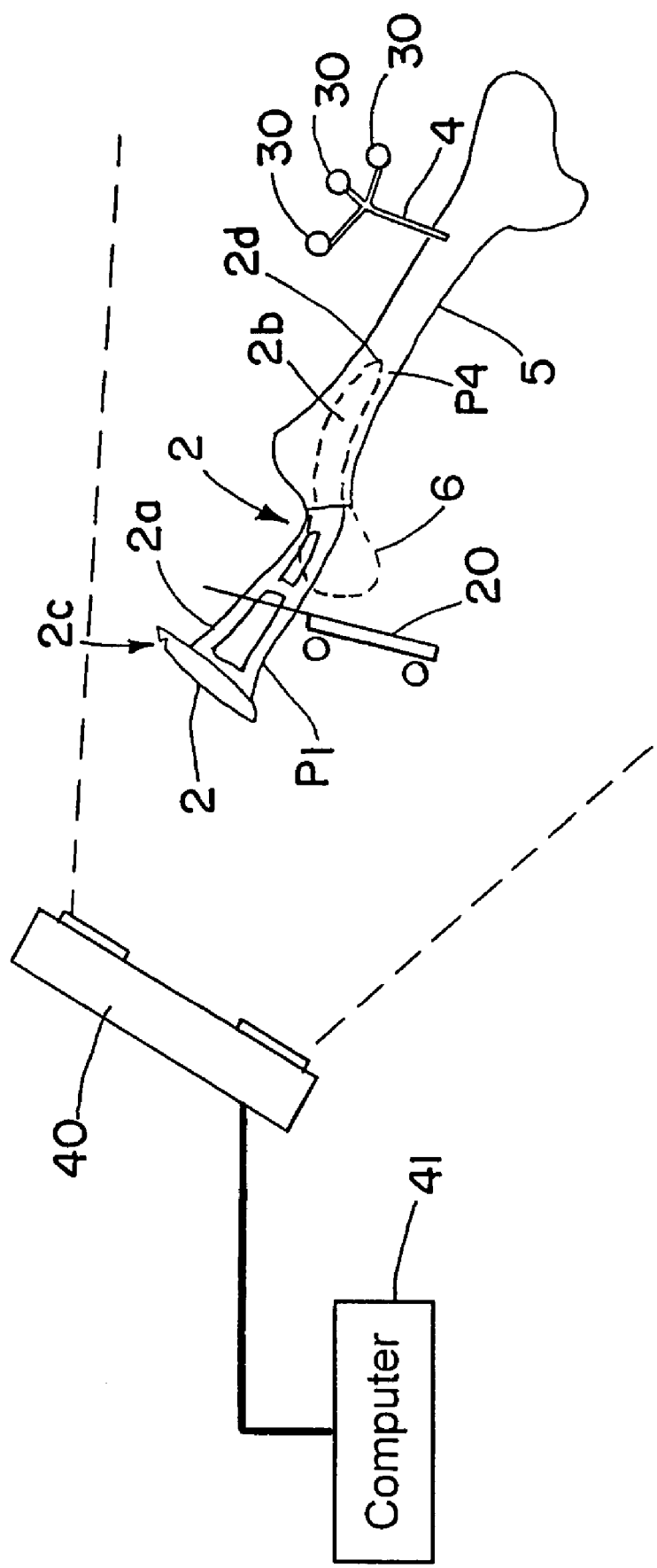
FIG. 2 shows an exemplary arrangement for determining the location of an instrument relative to a bone in accordance with the invention.

FIG. 2 shows an arrangement for determining the position of the instrument 2 relative to a bone 5, wherein the element 2b of the instrument 2 is placed within the bone 5. The example shown is intended to represent a hip operation in which the femoral head 6 has been resected. The second element 2b of the instrument 2 is formed as a broach and fixedly connected to the bone 5, such that the location of the instrument 2 is fixed relative to the bone 5. In this situation, the location of the instrument 2 relative to the bone 5, in particular the location of the hidden element 2b relative to the bone 5, for example, may be of interest to the surgeon. In particular, the location of the tip of the instrument 2 or the orientation of the plane P4 relative to the bone 5 may be of interest to the surgeon. The method, for example, allows the location of the plane P4 and/or the instrument tip 2d to be determined relative to the bone 5 in the situation shown in FIG. 2. This can be accomplished by measuring the relative location of one or more parts of the visible element 2a of the instrument 2 (e.g., plane P1), for example, by means of a pointer 20 that scans the plane P1 relative to the marker array 4. The camera 40 shown in FIG. 1 also can be used in the situation of FIG. 2, in order to detect the location of one part (plane P1) of the element 2a, as scanned using the pointer 20, relative to the marker array 4. The camera 40, together with the pointer 20, represents an example of a second detection means.

As shown in FIG. 2, a reference star 4 is attached to the bone 5. The reference star 4 can be fixed with regard to its location relative to the bone 5, e.g., the reference star 4 can be screwed into the bone 5. The relative location between the bone 5 and the reference star 4 preferably is known and stored. In order to determine the relative location, the bone 5 can be registered and/or calibrated together with the reference star 4, which represents an example of a marker array. This means that the bone 5 can be calibrated together with the markers 30 of the marker array 4, for example, by means of a CT (a three-dimensional x-ray recording), so as to determine the location of the markers 30 relative to parts of the bone 5. Determining the location by means of CT merely represents one example of a first detection means. Alternatively, determination of the location can be performed by scanning the surface of the bone 5 and also that of the markers spheres 30 of the marker array 4 by means of a pointer to determine the essential structure of the bone 5 and the relative location between the bone and the markers spheres connected to the bone. It is of course also possible to optically detect the bone 5 by means of one or more cameras together with the marker array 4.

As the starting situation for determining the location of the instrument 2, one then has data on the location of parts of the bone (e.g., the location of the longitudinal axis of the bone 5, the location of particular surface sections and/or points or planes of the bone 5) relative to the marker array 4.

In addition to the location of parts of the bone 5, the location of one or more parts of the (visible) element 2a can be determined, for example, using the pointer 20. This determination is preferably made, as stated above, when the instrument 2 is fixedly connected to the bone 5, and in particular the element 2b of the instrument 2 is inserted into the bone 5. The location can be determined relative to one or more parts of the bone 5 and/or relative to the marker array 4 and/or in a reference system that, for example, is spatially based (e.g., in an operating theater). The location of the parts of the bone 5 and/or of the markers of the marker array 4 also can be determined in the reference system, so as to determine the relative location of the accessible element relative to the marker array 4 and therefore relative to the bone 5. The location of parts of the (non-visible) element 2b preferably is not determined, since these are not accessible, or only with difficulty, using for example pointers. The term "visible" is used here in the sense that the element is accessible and/or suitable for calibrating the location of parts of the element, in particular for calibrating by means of location measuring devices or scanning means (e.g., pointers) which, for example, are to be moved by hand to scan and/or optically detect parts of the elements.

The situation in which the instrument 2 is fixed to the bone 5 and in particular an element of the instrument 2 (element 2b) is inserted into the bone 5 is referred to below as the fixed situation. In this fixed situation, the location of a part of the instrument 2, in particular the location of a part of the visible element 2a, can be determined relative to the marker array 4. In this respect, an accessible (also referred to as visible) element represents an example of an element that is calibrated in the fixed situation, wherein "calibrated" means that the location of one or more parts of the element has been measured in the fixed situation, in particular relative to the marker array 4. A non-accessible (non-visible) element here represents an example of an element that is not calibrated in the fixed situation, wherein "not calibrated" means that the location of one or more parts of the element have not been measured in the fixed situation, in particular could not be measured, and in particular have not been measured relative to the marker array 4.

In this fixed situation, the following information and also in particular data thus arise: the relative location of one or more predetermined parts of the bone 5 relative to the marker array 4 is known. Data on the relative location of one or more predetermined parts of an element of the instrument 2 that is calibrated in the fixed situation, relative to one or more predetermined parts of an element of the instrument 2 that is not calibrated in the fixed situation, are also known. The relative location of the one or more predetermined parts of the calibrated element relative to the marker array 4 is also known. The data and/or information thus known can be used to determine the relative location of the one or more predetermined parts of the bone 5 relative to the one or more predetermined parts of the non-accessible element of the instrument 2. It is thus in particular possible to determine the relative location of the predetermined part of parts of the non-calibrated element of the instrument 2 relative to the predetermined part of parts of the bone 5.

The determination preferably is made on the basis of a chain of relative locations (see FIG. 5) which read as follows: the relative location A between the bone 5 and the marker array 4 is known. The relative location B between the marker array 4 and the element 2a of the instrument 2 calibrated in the fixed state is known. The relative location C between the element 2a calibrated in the fixed state and the element of the instrument 2 which is non-accessible in the fixed state is known. This results in a chain of relative locations A, B and C which allows the relative location D between the bone 5 and the element 2b of the instrument 2 which is not calibrated in the fixed state to be calculated.

In the aforesaid chain of information, the location of the bone 5 preferably is defined by the predetermined parts of the bone 5, the location of the marker array 4 preferably is defined by the location of the markers of the marker array 4, and the location of the calibrated elements of the instrument 2 preferably is defined by the location of the predetermined parts of the elements. In order to calculate the relative location D, the relative locations A, B and C, for example, can be described by vectors, wherein a vector A points from the bone 5 to the marker array 4, a vector B points from the marker array 4 to the element 2a, and a vector C points from the element 2a to the element 2b. A vector D representing the relative location D then results from adding the vectors A, B and C. A calculation program can determine the relative location D by applying geometric laws.

FIGS. 3a and 3b show an alternative embodiment in which the location of parts of an element 2a of the instrument 2 is calibrated and determined. In FIGS. 3a and 3b, only the first element 2a of the instrument is calibrated. As in FIG. 1, pointers 20 comprising marker spheres 30 can be used in this respect to measure parts, in particular characteristic, predetermined parts of the element, such as for example planes and in particular the location of these predetermined parts relative to each other. The second element 2b of the instrument 2 is not shown in FIG. 3. The second element 2b can be detachably attached to the instrument 2, wherein a mechanism for attaching the second element 2b to the first element 2a preferably is configured such that the location of the first element 2a relative to the second element 2b is fixed and known in advance. In particular, it is only possible to fasten the second element 2b to the first element 2a in a location relative to the first element 2a which is known in advance. At least one relative location of a part of the second element 2b relative to at least one part of the first element 2a preferably is also known in advance. The first element 2a, for example, can then be used as a reusable handle, while the second element 2b is an exchangeable element, in particular exhibiting a predetermined shape.

FIGS. 4a and 4b show examples for determining the location of a plane that represents a part of an object or body structure. FIG. 4a shows a reference star 7, wherein a planar plate 70 is attached to the lower end of the reference star 7, stationary relative to the reference star 7. Using the planar plate 70, it is possible to detect the location of a plane 75 (indicated by a broken line) of an instrument or bone, for example, by placing the plate 70 full-face, in particular flush, onto the plane 75.

An alternative way of detecting the location of a plane 76 is shown in FIG. 4b. The tip of the pointer 20 can scan a number of points on the plane 76. With the aid of the markers 30, the position of which can be detected by a camera, the location of the plane 76 then can be determined in a reference system and/or relative to another part (of an object or body structure).

Figure 6:
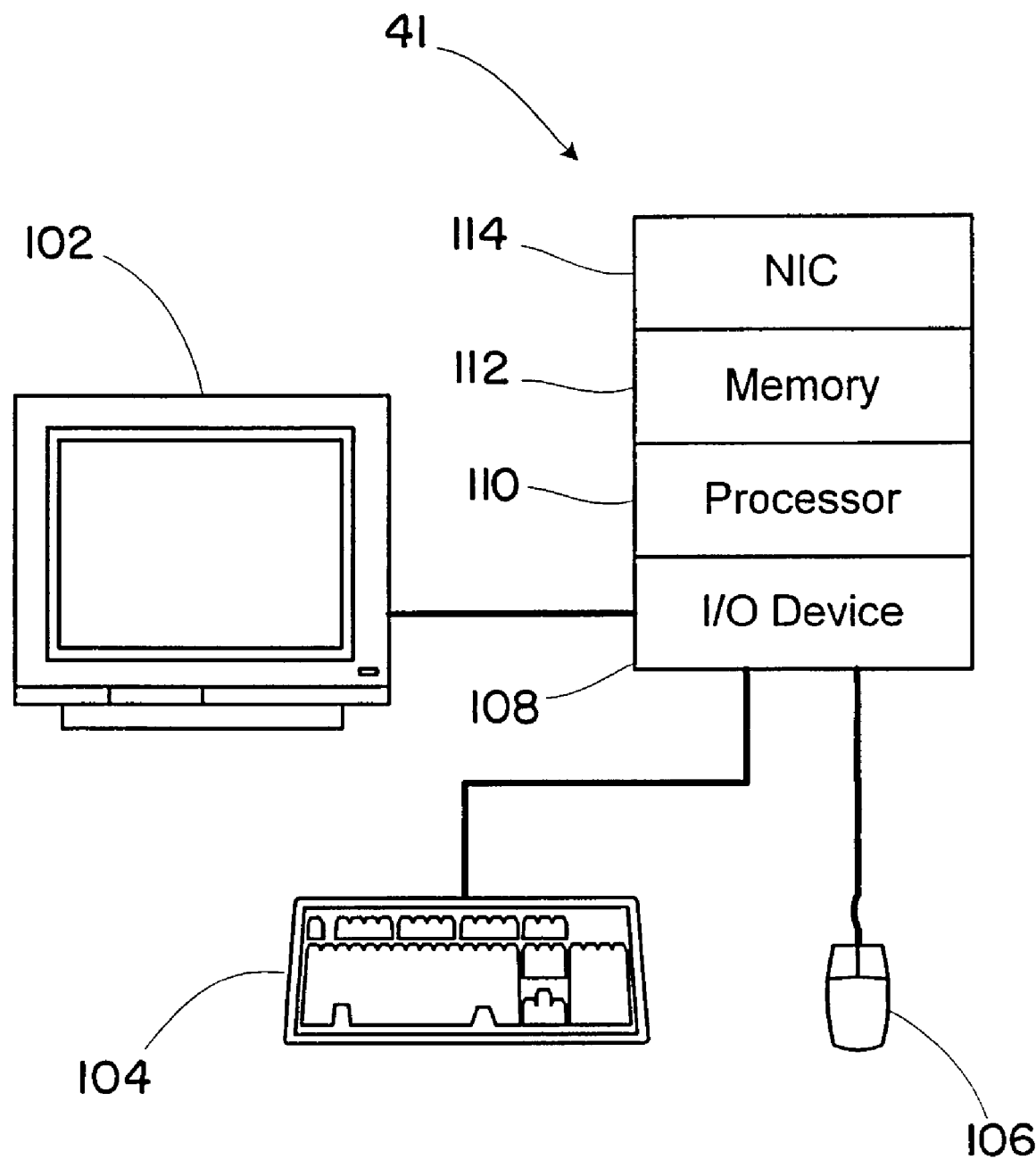
FIG. 6 is a block diagram of an exemplary computer system that can be used to carry out the method in accordance with invention.

Moving now to FIG. 6 there is shown a block diagram of an exemplary computer system 41 that may be used to implement one or more of the methods described herein. The computer system may be a stand alone system, or it may be part of the navigation system, detection system, or the like. The computer system 41 may include a display 102 for viewing system information, and a keyboard 104 and pointing device 106 for data entry, screen navigation, etc. A computer mouse or other device that points to or otherwise identifies a location, action, etc., e.g., by a point and click method or some other method, are examples of a pointing device 106. Alternatively, a touch screen (not shown) may be used in place of the keyboard 104 and pointing device 106. The display 102, keyboard 104 and mouse 106 communicate with a processor via an input/output device 108, such as a video card and/or serial port (e.g., a USB port or the like).

A processor 110, such as an AMD ATHLON 64® processor or an Intel PENTIUM IV® processor, combined with a memory 112 execute programs to perform various functions, such as data entry, numerical calculations, screen display, system setup, etc. The memory 112 may comprise several devices, including volatile and non-volatile memory components. Accordingly, the memory 112 may include, for example, random access memory (RAM), read-only memory (ROM), hard disks, floppy disks, optical disks (e.g., CDs and DVDs), tapes, flash devices and/or other memory components, plus associated drives, players and/or readers for the memory devices. The processor 110 and the memory 112 are coupled using a local interface (not shown). The local interface may be, for example, a data bus with accompanying control bus, a network, or other subsystem.

The memory may form part of a storage medium for storing information, such as application data, screen information, programs, etc., part of which may be in the form of a database. The storage medium may be a hard drive, for example, or any other storage means that can retain data, including other magnetic and/or optical storage devices. A network interface card (NIC) 114 allows the computer system 41 to communicate with other devices.

A person having ordinary skill in the art of computer programming and applications of programming for computer systems would be able in view of the description provided herein to program a computer system 100 to operate and to carry out the functions described herein. Accordingly, details as to the specific programming code have been omitted for the sake of brevity. Also, while software in the memory 112 or in some other memory of the computer and/or server may be used to allow the system to carry out the functions and features described herein in accordance with the preferred embodiment of the invention, such functions and features also could be carried out via dedicated hardware, firmware, software, or combinations thereof, without departing from the scope of the invention.

Computer program elements of the invention may be embodied in hardware and/or in software (including firmware, resident software, micro-code, etc.). The invention may take the form of a computer program product, which can be embodied by a computer-usable or computer-readable storage medium having computer-usable or computer-readable program instructions, "code" or a "computer program" embodied in the medium for use by or in connection with the instruction execution system. In the context of this document, a computer-usable or computer-readable medium may be any medium that can contain, store, communicate, propagate, or transport the program for use by or in connection with the instruction execution system, apparatus, or device. The computer-usable or computer-readable medium may be, for example but not limited to, an electronic, magnetic, optical, electromagnetic, infrared, or semiconductor system, apparatus, device, or propagation medium such as the Internet. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner. The computer program product and any software and hardware described herein form the various means for carrying out the functions of the invention in the example embodiments.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A method for determining a location of an object relative to a body structure, comprising:
  a) providing a location of a first point or first plane corresponding to a first part of the object relative to a second point or second plane corresponding to a second part of the object, said second part different from said first part;
  b) attaching a body marker device to the body structure;
  c) detecting a location of the body marker device relative to the body structure;
  d) positioning the object relative to the body structure;
  e) detecting a location of the first point or first plane relative to the body marker device, said detecting performed without using a marker array attached to the object; and
  f) calculating a relative location of the second part of the object relative to the location of the body structure based on the location of the first point or first plane relative to the second point or second plane, the location of the body marker device relative to the body structure, and the location of the first point or first plane relative to the body marker device.

2. The method according to claim 1, wherein the object is a medical instrument at least partially situated inside the body structure.

3. The method according to claim 1, wherein providing the location of the first point or first plane relative to the second point or second plane includes measuring the location of the first point or first plane relative to the second point or second plane.

4. The method according to claim 1, wherein the object comprises at least a first element and a second element, wherein the first part is a part of the first element, and the second part is a part of the second element.

5. The method according to claim 4, wherein the second element is removably attachable to the first element such that a relative location between the first part and the second part is known prior to attachment of the second element to the first element.

6. The method according to claim 1, wherein detecting a location of the first point or first plane relative to the body marker device includes optically detecting a location of the first point or first plane relative to the body marker device.

7. A system for determining a location of an object relative to a body structure, comprising:
   a) a device for providing a location of a first point or first plane corresponding to a first part of the object relative to a second point or second plane corresponding to a second part of the object, said second part different from the first part;
   b) a body marker device;
   c) a first detection device for detecting a location of the body marker device relative to the body structure when the body marker device is stationary relative to the body structure;
   d) a second detection device for detecting a location of the first point or first plane relative to the body marker device; and
   e) a computational unit configured to calculate, without using a marker device attached to the object, a location of the second part of the object relative to the location of the body structure, said calculation based on the location of the first point or first plane relative to the second point or second plane, the location of the body marker device relative to the body structure, and the location of the first point or first plane relative to the marker device.

8. The system according to claim 7, wherein the device for providing the location of the first point or first plane relative to the second point or second plane comprises a storage device, and the location of the first point or first plane relative to the second point or second plane is stored on the storage device.

9. The system according to claim 7, wherein the object comprises at least a first element and a second element, wherein the first part is a part of the first element, and the second part is a part of the second element.

10. The system according to claim 9, wherein the second element is removably attachable to the first element such that a relative location between the first part and the second part is always the same.

11. The system according to claim 7, wherein the body marker device is configured to be attachable to the body structure.

12. The system according to claim 7, wherein the object comprises an identifier corresponding to the first point or first plane for applying a scanning device onto the object.

13. The system according to claim 7, wherein the device for providing a location of a first point or first plane relative to a second point or second plane comprises a memory operative to store the location of the first point or first plane relative to the second point or second plane of the object.

14. The system according to claim 7, wherein the device for providing a location of a first point or first plane relative to a second point or second plane comprises a measuring device operative to measure the location of the first point or first plane relative to the second point or second plane.

15. The system according to claim 7, further comprising a camera system configured to optically detect a location of the device for providing a location of the first point or first plane relative to the second point or second plane.

16. A computer program embodied on a non-transitory computer readable storage medium for determining a location of an object relative to a body structure, wherein a body marker device is attached to the body structure, and said object is positioned relative to the body structure; comprising:
   code that provides a location of a first point or first plane corresponding to a first part of the object relative to a second point or second plane corresponding to a second part of the object, said second part different from said first part;
   code that detects a location of the body marker device relative to the body structure;
   code that detects a location of the first point or first plane relative to the marker device; and
   code that calculates, without using a marker device attached to the object, a relative location of the second part of the object relative to the location of the body structure, said calculation based on the location of the first point or first plane relative to the second point or second plane, the location of the marker device relative to the body structure, and the location of the first point or first plane relative to the marker device.

* * * * *